(12) United States Patent
Hopper

(10) Patent No.: US 6,182,660 B1
(45) Date of Patent: Feb. 6, 2001

(54) NON-INVASIVE SINUS PAIN RELIEVING ASSEMBLY

(76) Inventor: William J. Hopper, 1270 N. Marine Dr., 101-233, Tamuning, GU (US) 96911

(*) Notice: Under 35 U.S.C. 154(b), the term of this patent shall be extended for 0 days.

(21) Appl. No.: 09/028,873

(22) Filed: Feb. 22, 1998

(51) Int. Cl.⁷ ................................................. A62B 18/02
(52) U.S. Cl. ............................ 128/207.13; 128/200.24; 606/1
(58) Field of Search .................. 128/203.29, 204.28, 128/205.25, 207.13, 200.22, 200.24, 201.23, 201.24, 203.28, 205.13, 205.16, 205.17, 206.12, 206.21, 206.24, 206.28; 604/36, 94; 606/201, 191, 196

(56) References Cited

U.S. PATENT DOCUMENTS

| | | | |
|---|---|---|---|
| 743,294 | * 11/1903 | Knowles | 128/203.29 |
| 2,428,451 | * 10/1947 | Emerson | 128/205.13 |
| 2,485,184 | * 10/1949 | Blackman et al. | 604/94 |
| 2,737,177 | * 3/1956 | Anklin | 128/205.13 |
| 3,667,463 | * 6/1972 | Barnes | 128/203.16 |
| 4,403,611 | 9/1983 | Babbitt et al. | |
| 4,498,472 | * 2/1985 | Tanaka | 128/203.28 |
| 4,817,626 | 4/1989 | Blaine | |
| 4,934,359 | 6/1990 | Blaine | |
| 4,995,386 | 2/1991 | Ng | |
| 5,024,612 | * 6/1991 | Honert et al. | 604/36 |
| 5,024,653 | 6/1991 | Kohnke | |
| 5,062,835 | 11/1991 | Maitz et al. | |
| 5,098,386 | 3/1992 | Smith | |
| 5,114,415 | 5/1992 | Shedlock | |
| 5,318,548 | 6/1994 | Filshie | |
| 5,431,636 | 7/1995 | Stangerup | |
| 5,527,275 | 6/1996 | Ginsberg | |
| 5,599,332 | 2/1997 | Cashel | |

FOREIGN PATENT DOCUMENTS

2182249  * 5/1987 (GB) ............................... 128/203.28

* cited by examiner

Primary Examiner—Glenn K. Dawson
(74) Attorney, Agent, or Firm—Malloy & Malloy, P.A.

(57) ABSTRACT

A lightweight, portable non-invasive device specifically designed to regulate and effectively equalize the pressure between the sinus cavities and middle ear, and the nasal cavity and nasopharynx. The relieving of the pressure within the sinus cavities in turn relieves pain normally associated with such a condition. The subject pressure equalizing assembly has a face mask having a seal disposed about the outer periphery thereof which is specifically dimensioned and configured to surround the nose and nostrils of the user in an outwardly spaced relation thereto. This seal effectively isolates the nasal cavity and nasopharynx when the user swallow, and defines direct fluid communication with a vacuum chamber and a pressure regulating assembly serving to create an initial negative pressure within the nasal cavity and nasopharynx. Fluid in the form of mucous, liquid and/or air is transferred from the sinus cavities which may define a zone of relative high pressure such that the pressure is effectively regulated between the sinus cavities, middle ear, nasal cavities and nasopharynx through the selective manipulation of the pressure regulating assembly thereby providing immediate relief from sinus pain while helping to relieve middle ear pressure and associated symptoms.

25 Claims, 7 Drawing Sheets

NON-INVASIVE SINUS PAIN RELIEVING ASSEMBLY

BACKGROUND OF THE INVENTION

1. Field of the Invention

This invention relates to a non-invasive sinus pain relieving assembly specifically structured to equalize the pressure between the sinus cavities and the middle ear by isolating the nasal cavities and nasopharynx and subjecting this area to a negative pressure thereby providing immediate relief of normally involved sinus pain, and helping to release trapped middle ear pressure.

2. Description of the Related Art

Currently, there is no commercially available, portable product or device available to the general public without a prescription that mechanically but non-intrusively relieves sinus and middle ear pressure. Present methods of treatment of sinus pain are often chemically related such as numerous vasoconstricting local agents or prescription drugs. Indeed, chemical dependency due to the large numbers of vasoconstrictors in use is very wide spread. In addition, tissue damage from the improper and excessive use of these vasoconstricting chemicals may lead to corrective surgery that is sometimes followed by required cosmetic surgery. Of course, surgery in the sinuses and nasal cavity can easily lead to the spread of infectious agents not only to the sensitive membranes involved but also to the bones forming these cavities.

Specifically, each sinus cavity is lined with a mucous membrane which are continuous with the mucous membrane of the nose and throat. When the nose and nasal cavity fail to produce enough mucous, the sinuses are triggered to overcompensate and make up the difference. Normally, the mucous from the sinuses drain into the nasal cavity through small apertures connecting the two areas. However, if the mucous membrane of the sinuses swells or mucous thickens due to improper hydration, drainage may be impeded. If this happens, pressure inside the sinus cavities may be trapped. This could cause a differential pressure to exist, squeezing sensitive nerves and possibly causing severe headaches or toothaches. This condition is called barotrauma. Furthermore, if outside barometric pressure increases because of normal weather movement, or with a change in altitude, as in a descending aircraft, auto or during recreation, the condition will worsen. The same condition may effect the middle ears if the bony cartilages of the eustachian tubes becomes obstructed with fluids restricting the equalizing of pressure in the middle ear, additionally referred to as aero otitis media.

When these conditions are encountered the sinuses and/or middle ear are subject to the above from numerous sources. The increasing outside pressure communicating with the nasal cavity, and nasopharynx will try to push into the now trapped low pressure sinus or middle ear through its normal drain apertures, reversing the flow of mucous. Upon this occurring, pressure cannot now be effectively equalized by fluid transfer from a sinus and/or middle ear zone of low pressure, to the nasal cavity and nasopharynx zone of high pressure. As is well accepted, fluid will have a tendency to move from a zone of high pressure to a zone of low pressure.

The slight increase in ambient pressure on the body causes a greater pressure differential between the blood in the swollen sinus tissues and the trapped lower pressure inside the sinus cavity. Additional swelling will therefore occur in the sinus tissue. In the middle ear the tympanic membrane or ear drum is pushed in by the higher outside pressure. This pressure differential will also cause an increase in blood flow to and distortion of the inner ear. Sensitive nerves in this inner ear area will be effected leading to possible pain and/or temporary hearing impairment or both. Of course the actual effects to the human body will vary depending on the size of the pressure differential as set forth above and the duration that such pressure differential is allowed to continue. However, the stress on these delicate membranes opens the door for bacterial infection that can lead to numerous well recognized complications.

Accordingly, there is a need for a mechanically operable, non-intrusive device that allows for the rapid release of trapped pressure in the sinus cavities and middle ear thereby serving to equalize the pressure in these zones by taking advantage of the physiological fact that all paranasal sinuses open into the lateral wall of the nasal cavity by means of small apertures to allow for the normal passage or drainage of mucous and accordingly sinus pressure. The middle ear similarly communicates with the nasopharynx by means of the eustachian tube, to drain fluids and maintain a pressure balance with the nasopharynx. A preferred mechanically operable device to accomplish the equalization of pressure will isolate the nasal cavity from ambient pressure conditions and establish fluid communication between the rapid acting and easily manipulatable pressure regulating structure which will serve to reduce the pressure in the nasal cavity and the nasopharynx thereby forcing the transfer of fluid from the now high pressure zones of the sinus cavities and/or middle ear causing the desired equalization of pressure.

SUMMARY OF THE PRESENT INVENTION

The present invention relates to a portable, non-invasive sinus pain relief assembly specifically structured to relieve sinus pain through the equalization of pressures between the sinus cavities and the nasal cavity and/or nasopharynx. Common to all of the preferred embodiments, to be described in greater detail hereinafter is the utilization of a mask having a body portion with a hollow interior and a continuous seal structure extending about the outer periphery of the mask. The seal is specifically structured and disposed to define sealing engagement with the face of the user in a surrounding area about the nose and nostrils of the user, and in somewhat outwardly spaced relation thereto, so as to avoid any type of intrusive penetration of the nasal cavity through the nostrils. By establishing the surrounding seal of the present invention, the nasal cavity and associated nasopharynx are isolated from ambient pressure, particularly when the uvula end of the soft palate is forced to rotate rearwardly into engagement with the back portion of the nasopharynx to create a separate pressure chamber of the nasopharynx and nasal cavity. Movement of the uvula in the manner described is accomplished by the patient swallowing while the face mask is in sealing engagement in the aforementioned operative position.

The present invention further comprises a pressure regulating assembly including a vacuum chamber selectively positionable between a collapsed position and an expanded position. The vacuum chamber is connected in preferably direct fluid communication to the inner end of the body portion of the face mask and accordingly in direct fluid communication with the interior of the nasal cavity and nasopharynx when the aforementioned seal of the mask is disposed in sealing engagement surrounding and effectively isolating the nasal cavity. The pressure regulating assembly is further structured to be selectively manipulated by the hands of the user so as to cause positioning of the vacuum chamber, and parts associated therewith, between the aforementioned collapsed position and expanded position. When in the collapsed position, a minimal amount of air is present within the vacuum chamber. To the contrary, when in the expanded position, the interior volume of the vacuum chamber increases forcing a flow of air from the interior of the mask, and as a result from the interior of the nasal cavity into and/or towards the interior of the vacuum chamber. The result is an initial creation of a negative pressure within the nasal cavity and nasopharynx when the soft palate is forced into engagement with a back portion of the nasopharynx to isolate such cavities. Due to the natural phenomenon of the tendency of fluid to travel from a zone of high pressure towards a zone of low pressure, the initial creation of negative pressure within the nasal cavity will force fluid flow mucous and air through the passages normally interconnecting the sinus cavities with the nasal cavity. Similar fluid flow will result between the cavities of the middle ears and the nasopharynx. The result of course will be an equalization of pressure and the immediate relief of pain caused by swelling and the existence of high pressure in the aforementioned middle ear and/or sinus cavities.

In accomplishing the above results, the present invention contemplates a first preferred embodiment wherein the pressure regulating assembly comprises a flexible material bellows having a hollow interior and positionable between the aforementioned outwardly expanded position and inwardly collapsed position. The inherent flexibility from which the bellow is formed serves to normally bias the bellows into the outwardly expanded position. An inwardly directed force or pressure exerted on the outer end of the bellows will cause its positioning into the collapsed position. This will vacate the majority of air within the vacuum chamber which is defined by and within the hollow interior of the bellows. The bellows has its inner or proximal end connected in direct fluid communication with the hollow interior of the mask and accordingly in direct fluid communication with the nasal cavity when the aforementioned peripheral seal on the mask is in sealing engagement and in surrounding relation to the nose and nostrils of the patient. As such, a release of the bellows by the user automatically forces the bellows into the outwardly expanded position due to the inherent flexibility of the bellows as set forth above. This in turn will cause a flow of air from the sealed interior of the mask and accordingly from the nasal cavity itself into the vacuum chamber on the interior of the bellows. An initial negative pressure will result in the interior of the nasal cavity causing any fluid (mucous, liquid and/or air) to flow from the now high pressure zone of the sinus cavities and middle ears into the now low pressure zone of the nasal cavity and nasopharynx through connecting passages and apertures. The pressure in the nasal cavities and/or middle ears will therefore be effectively equalized with the pressure in the nasal cavity and nasopharynx resulting in a relief of any pain caused by the existing increased pressure in the nasal cavity and middle ears.

Yet another preferred embodiment of the present invention is defined by a somewhat similar structure as the above noted first embodiment but differs therefrom by incorporating a housing to substantially surround the bellows and allow its movement between the aforementioned expanded position and collapsed position. Further, a positioning member is attached to the outer or distal end of the bellows and is contacted or engaged by the user when a force is desired to be applied to the bellows to move it from its outwardly expanded position to its inwardly collapsed position.

The housing further includes a lock assembly mounted at least partly thereon and partly on the positioning member such that cooperative components of the subject lock assembly serve to removably retain the bellows in its collapsed position when the components of the lock assembly are engaged with one another. Accordingly, the bellows, through manipulation of the positioning member, may be selectively moved into its collapsed position prior to the face mask being disposed in sealed engagement about the nose and nostrils of the user. Once the bellows is retained in its collapsed position by interaction of the components of the lock assembly, the face mask may be sealed in the desired and intended position. When the seal is accomplished, a release assembly may be activated which serves to separate or disengage the components of the lock assembly causing the bellows to automatically move into its outwardly expanded position without further manipulation by the hands of the user. The aforementioned negative pressure is initially formed in the nasal cavity, as described above with reference to the other preferred embodiment of the present invention.

Yet another preferred embodiment of the present invention comprises the pressure regulating assembly being defined by a piston movably mounted within a housing wherein the interior of the housing defines the vacuum chamber. As with the previous preferred embodiments, the piston is movable between an outwardly extending, expanded position and an inwardly disposed, collapsed position. The piston is normally biased to its outwardly expanded position by the existence of a biasing spring located within the vacuum chamber and positioned and structured to accomplish such biasing. A positioning member is movably connected to the piston and is structured to move along a specific path or track formed in the housing and when so moving force the piston from the outwardly expanded position to the inwardly collapsed position. Additional structural features of the positioning member and housing relative to the travel of the piston include an automatic release of the piston once the positioning member reaches an effective bottom of its inwardly directed stroke. When such occurs the piston is automatically released from its collapsed position towards and into its outwardly expanded position to accomplish the aforementioned initial negative pressure within the nasal cavity. A positioning member is then disposed in its outermost extended position to again assume its engagement with the piston for repeated positioning of the piston into its collapsed position. Travel of the piston between the collapsed and expanded positions should occur when the face mask has established its sealing engagement about the nose and nostrils of the face of the user. A vent assembly is formed on the body and is associated with a valve structure specifically configured to allow the venting of air from the vacuum chamber as the piston travels from the outwardly expanded position to the collapsed position. The vacuum chamber is of course connected in direct fluid communication with the interior of the body of the mask so as to cause the flow of air from the nasal cavity, through the hollow interior of the mask into the vacuum chamber, thereby defining the formation of the initial negative pressure with the nasal cavity.

The factors set forth above creating pain within the sinus cavities can easily be compounded due to a lack of proper hydration in the nasal cavity and other affected areas. Accordingly, the present invention further contemplates an additional preferred embodiment in the form of an attachment to the other structural components indicated above that allows steam or heated water vapor or saline solution to "pre-humidify" the nasal cavity and nasopharynx under ambient conditions prior to the invention's use and operation to affect a lower pressure in the sinus cavities and middle ear. More specifically, a hydrator assembly comprises a housing having a hollow interior in which heated water or saline solution is placed in order to accomplish the hydration process. The upper end of the hydrator housing includes an opening and surrounding fitting which is adaptable for sealing engagement with the interior of the face mask so as to establish direct fluid communication with the interior of the hydrator housing and the interior of the face mask body. A hand manipulated valve structure is mounted on the hydrator housing and serves to selectively segregate or establish communication between the interior of the hydrator housing and the interior of the mask. In operation, the heated water vapor or steam from the heated water in the interior of the hydrator housing rises upwardly through the opening of the top of the housing when the aforementioned valve structure is in its opened position. The water vapor passes into the interior of the mask and eventually into the nasal cavity and nasopharynx. The above set forth "pre-hydration" process occurs when the face mask is sealed about the nose and nostrils of the user and the pressure regulating assembly is disposed in its collapsed position.

It is an object of the present invention to provide a non-invasive sinus pain relief assembly which is compact and portable, yet which is highly effective by addressing a primary source of common sinus pain.

A further object of the present invention is to provide a sinus pain relief assembly which does not require any chemical components in order to relieve sinus pain.

An added object of the present invention is to provide a sinus pain relief assembly which is structured to be maintained in an operative, collapsed position upon engagement with a user's face so as to prevent the introduction of air into the nasal passages upon the operation of the assembly.

Also an object of the present invention is to provide a sinus pain relief assembly which is highly effective, yet which operates in a non-invasive manner.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
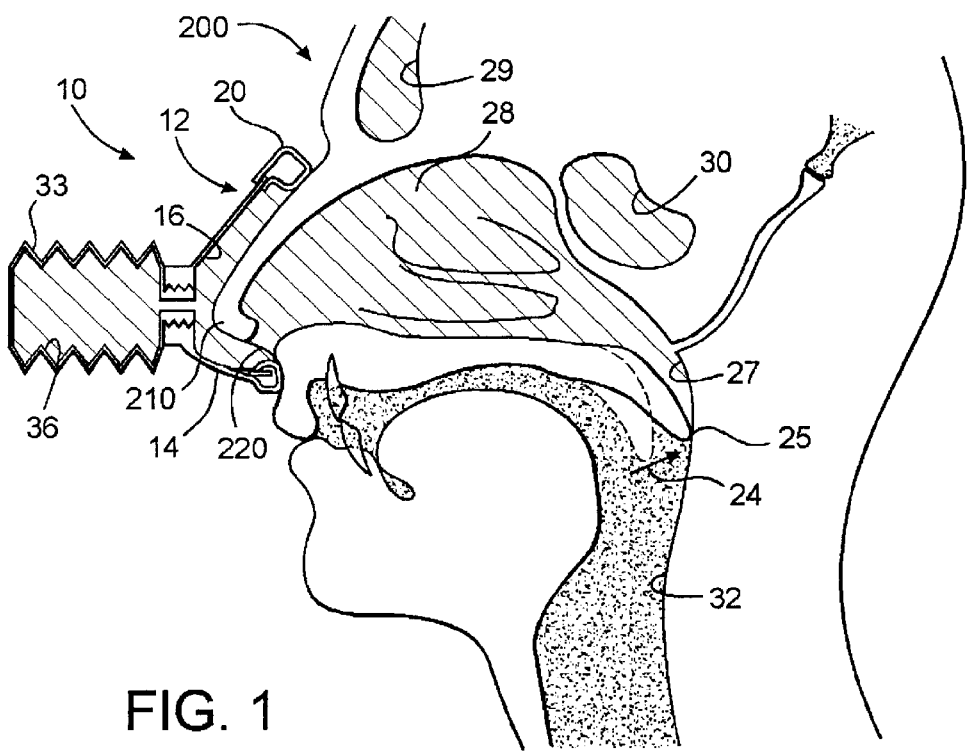
FIG. 1 is a schematic view in partial section indicating the nasal cavity, nasopharynx and sinus cavity and their effective pressurization during operation of the subject invention.
Figure 2:
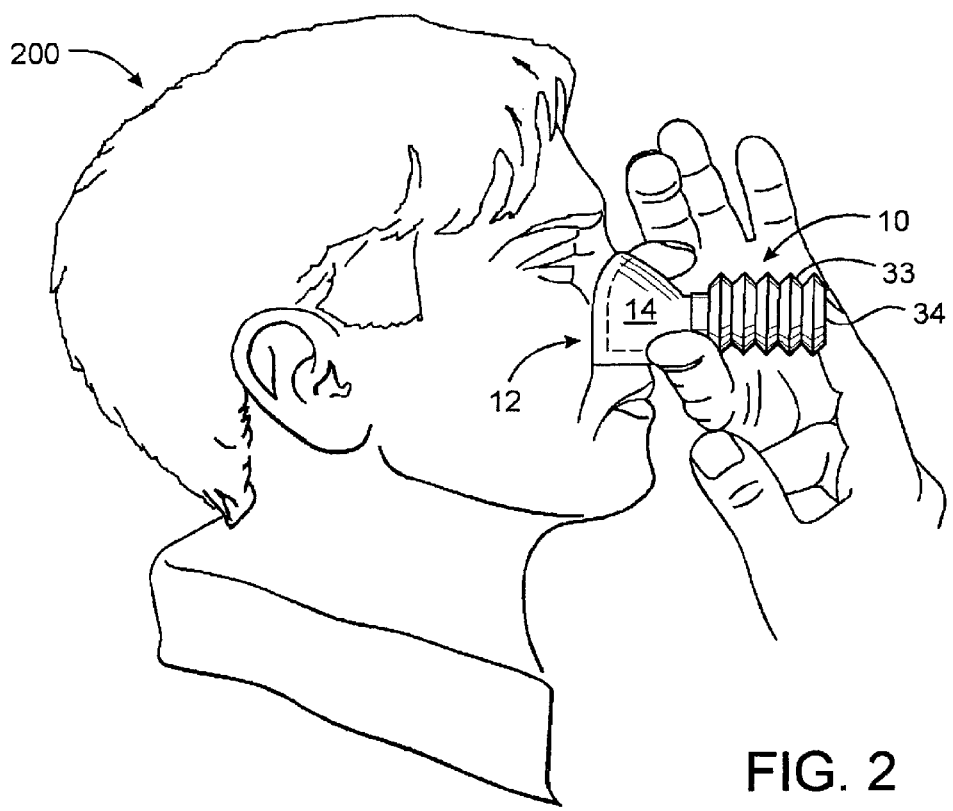
FIG. 2 is a side view in partial perspective showing one preferred embodiment of the present invention in an operative position on a user.

The present invention is directed towards a non-invasive sinus pain relief assembly having one preferred embodiment thereof generally indicated as 10 and shown in an operative position in FIGS. 1 and 2. More specifically, with reference to FIG. 1 the various effective cavities of the patient or user of the subject assembly 10 are delineated for purposes of explanation. The assembly 10 includes a preferably small, mask, generally indicated as 12, having a body portion 14 with a hollow interior as at 16. The outer end of the body portion 14 includes a continuous peripheral seal as at 20 designed to create a seal on the face of the user 200. More specifically, a fluid seal is created in surrounding relation to the nose 210 and an outwardly spaced relation to the nostrils 220. An important feature of the present invention is the preferred structuring of the preferred embodiments herein so as to be non-invasive in that operation of the subject assembly 10 as well as the other preferred embodiments occurs without entering the nasal cavity per se through the nostrils 220. Moreover, while any preferably resilient material seal 20 can be employed to achieve mating, generally air-tight engagement with the face and nose of a user, in a preferred embodiment the seal 20 is formed from a self conforming material such as hydro-plastic. Specifically, the entire mask 12 or merely the seal portion thereof can be conforming of this self conforming material, such that a user can conform the seal 20 to the contours of their face, and can achieve a more fluid impervious engagement. Typically, such molding can be achieved either by placing the mask 12 on the users face, or with some materials, by heating or otherwise treating the material to permit the conforming. Such an embodiment is particularly suited when the device is to be used by many individuals, which each individual having there own detachable mask 12.

Again with reference to FIG. 1 the directional arrow as at 24 serves to indicate the rearward rotation of the uvula 25 located at the end of the soft palate into engaging and somewhat sealing relation to the back of the nasopharynx generally as at 27. Further, the nasal cavity 28 as well as the indicated sinus cavities 29 and 30 are effectively isolated from the lower part of the esophagus 32 and from exterior ambient pressures through the mouth and oral cavity and also through the nostril 220. This isolation occurs due to the rearward rotation of the uvula 25 into engagement with the back of the nasopharynx 27 and also the existence of the sealing engagement of the peripheral seal 20 in surrounding and spaced relation to the nose 211 and nostrils 220 of the user 200.

Figure 3:
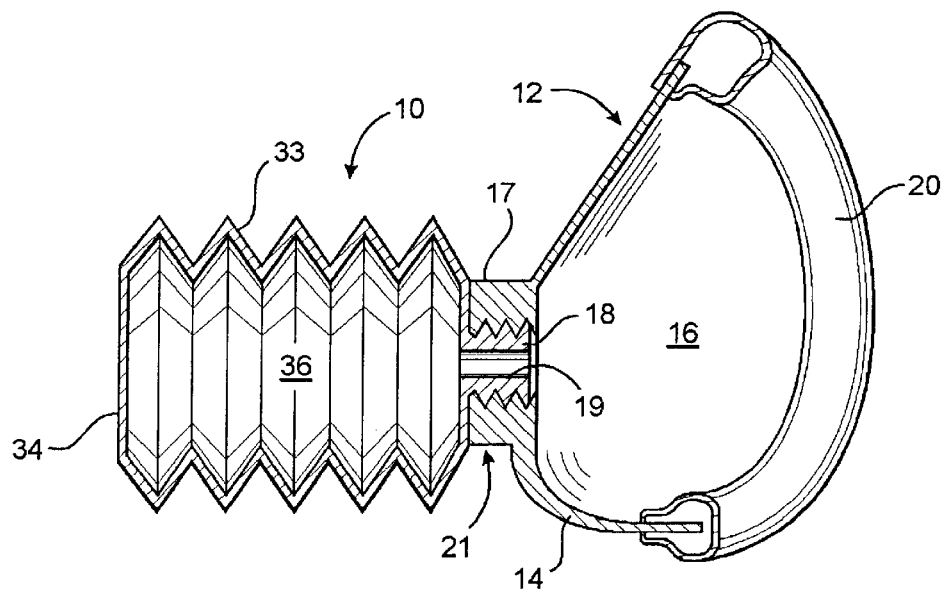
FIG. 3 is a sectional view of the assembled components of the embodiment of FIG. 2.

As will be explained in greater detail hereinafter, the sinus pain relief assembly in the embodiments of FIGS. 1–4 includes a pressure regulating assembly in the form of bellows 33. The bellows 33 are formed from a flexible plastic or like material which is inherently biased to assume the outwardly expanded position as shown in FIGS. 1, 2 and 3, and may include a resilient material bulb or a piston structure. A preferably threaded connector structure as at 35 serves to removably connect the inner or proximal end of the bellows 33 at the inner end of the body portion 14 and in direct fluid communication with the hollow interior 16 of the body portion 14 of mask 12.

The placing of an inwardly directed pressure by the user 200, such as by utilizing their finger, (See FIG. 2) on the outer or distal end 34 of the bellows 33 will cause it to move from the outer, expanded position, where a maximum amount of air is contained within the vacuum chamber 36 defined within the interior of the bellows 33, to an inwardly directed collapsed position, wherein a minimal amount of air is contained within the vacuum chamber 36. Preferably, this collapsed position is achieved before the assembly 10 is sealed against the user's face. When the hollows 33 is positioned in its collapsed position and once the seal 20 is in sealing engagement about the nose 210 and nostrils 220 of the user 200, the patient facilitates isolation of the lower esophagus 32 by swallowing. Swallowing causes the rearward rotation, in accordance with the directional arrow 24, of the end of the soft palate 25 into engagement with the nasopharynx 27. Indeed, once sealed against a user so as to enclose the nose, there is a low pressure state inside the sinus cavities and nasopharynx, and there is insufficient air movement to move liquids into the assembly 10. As the bellows moves to the expanded position shown in FIGS. 1 and 3, a flow of air, which was under negative tension, will be caused to travel from the interior of the nasal cavity 28 into the hollow interior 16 of the body portion 14 and eventually into the interior of the vacuum chamber 36 of bellows 33. This will initially cause a negative pressure within the nasal cavity 28 and nasopharynx 27. Due to normally existing passages and apertures existing between the sinus cavities 29 and 30 and the nasal cavity 28, the initial negative pressure within the nasal cavity 28 will cause a flow of fluid (mucous, liquid, air) from what may be a now existing high pressure zone in the sinus cavities 29 and 30 into the now low pressure zone of the nasal cavity 28 through the aforementioned interconnecting passages and apertures. The pressure will thereby be equalized between the nasal cavity 28 and the sinus cavities 29 and 30. For purposes of disclosure certain linear cross hatching existing in FIG. 1 represents the initial negative pressure being exerted on the nasal cavity 28 and effectively on the sinus cavities 29 and 30 as the vacuum chamber 36 and bellows expand from its collapsed position to the pictured, expanded position shown in FIGS. 1 and 3. After use by an individual, the assembly 10 can be removed from its operative position by simply swallowing when it is under a negative pressure state.

Figure 4:
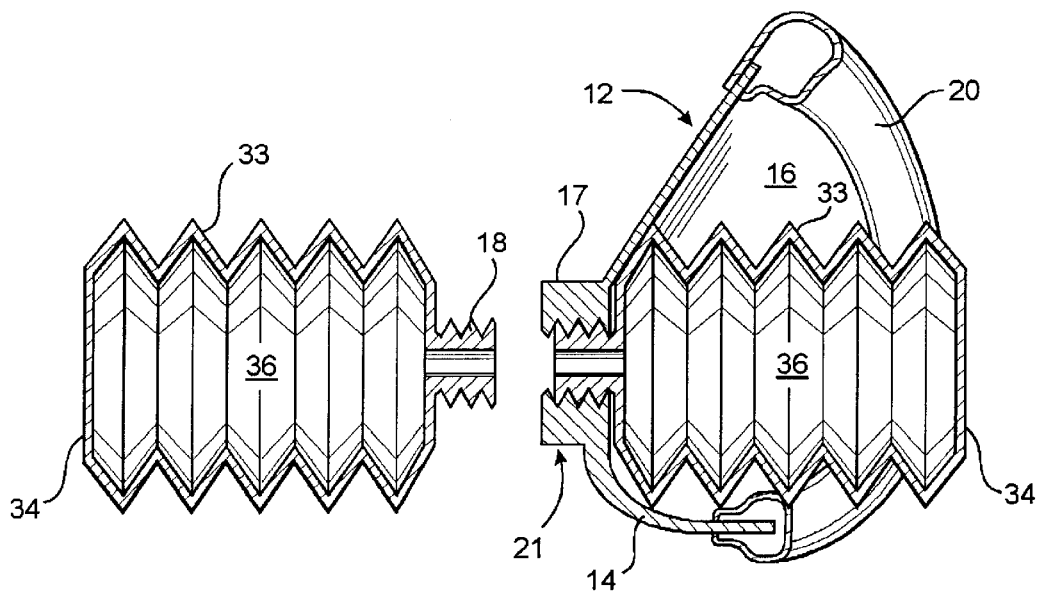
FIG. 4 is a sectional view in detached and exploded form of the embodiment of FIG. 2.

With reference to FIGS. 3 and 4, the preferred embodiment of the present invention further comprises a connector 21, preferably defined by a female, internally threaded collar 17 integrally formed on one end of the body portion 14 and specifically structured to be removably connected to an externally threaded male member 18 preferably integrally formed on the inner or proximal end of the bellows 33. A passage as at 19 is formed within the male member 18 so as to establish direct fluid communication between the hollow interior 16 of the body portion 14 and the vacuum chamber 36 defined on the interior of the bellows 33.

With reference to FIG. 4, the connector 21 is preferably removably connected so as to allow detachment of the male member 18 from the female collar 17 and from its operative position into a stored position wherein the bellows 33 is removably secured and disposed in the hollow interior 16 of the body portion 14 as shown.

Figure 5:
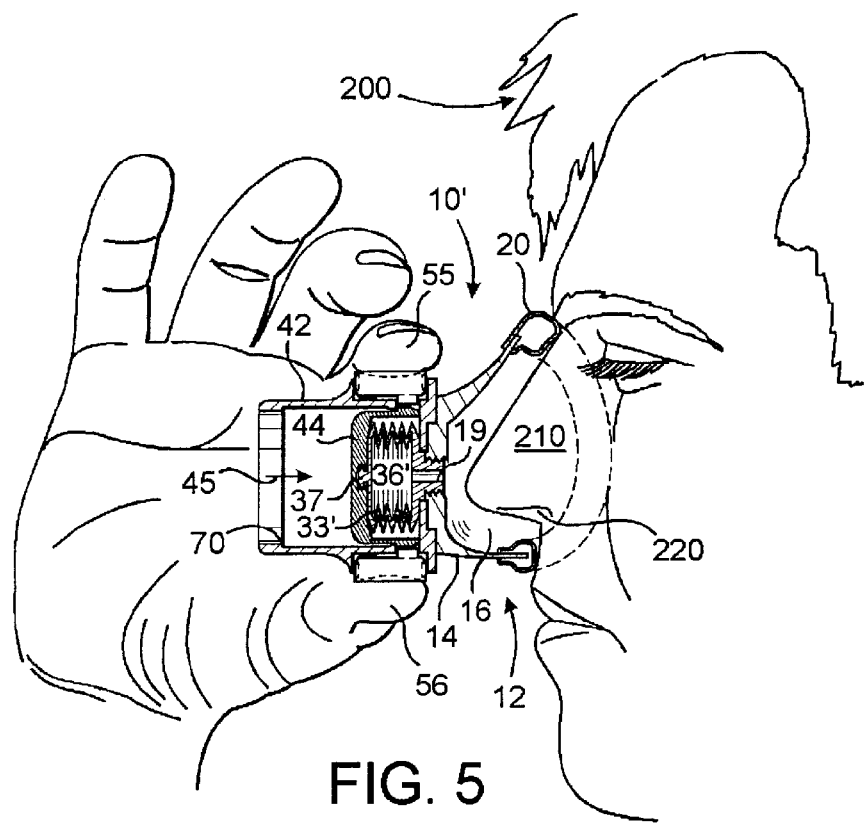
FIG. 5 is side view in partial section of yet another preferred embodiment of the present invention in an operative position on the face of the user.
Figure 6:
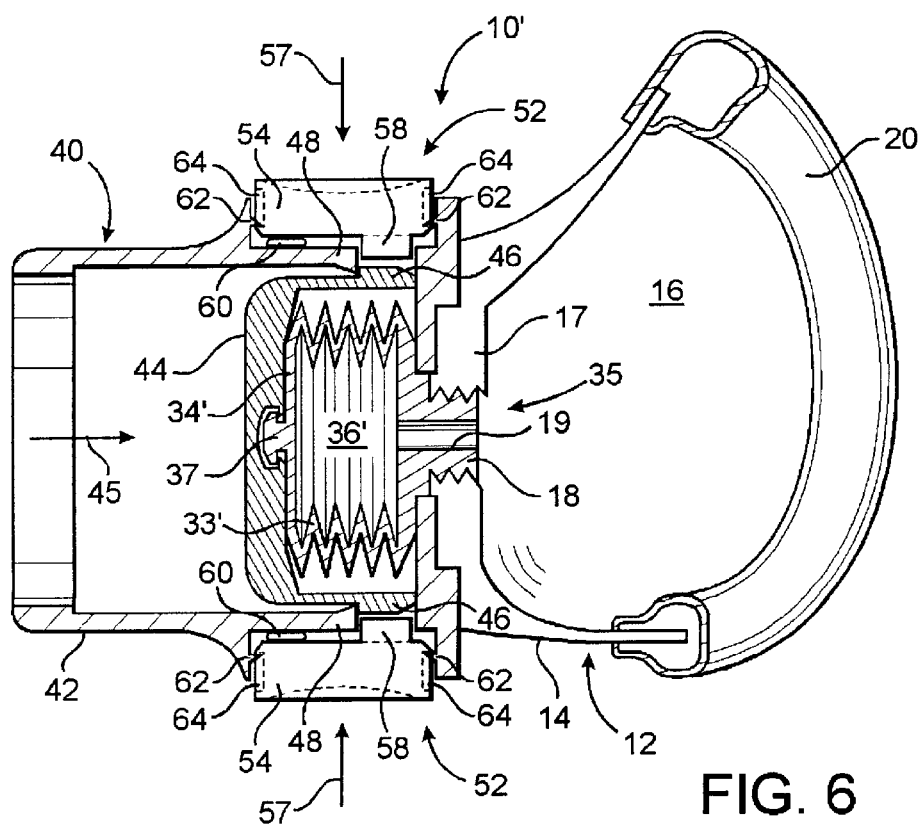
FIG. 6 is a detailed sectional view of the embodiment of FIG. 5.
Figure 7:
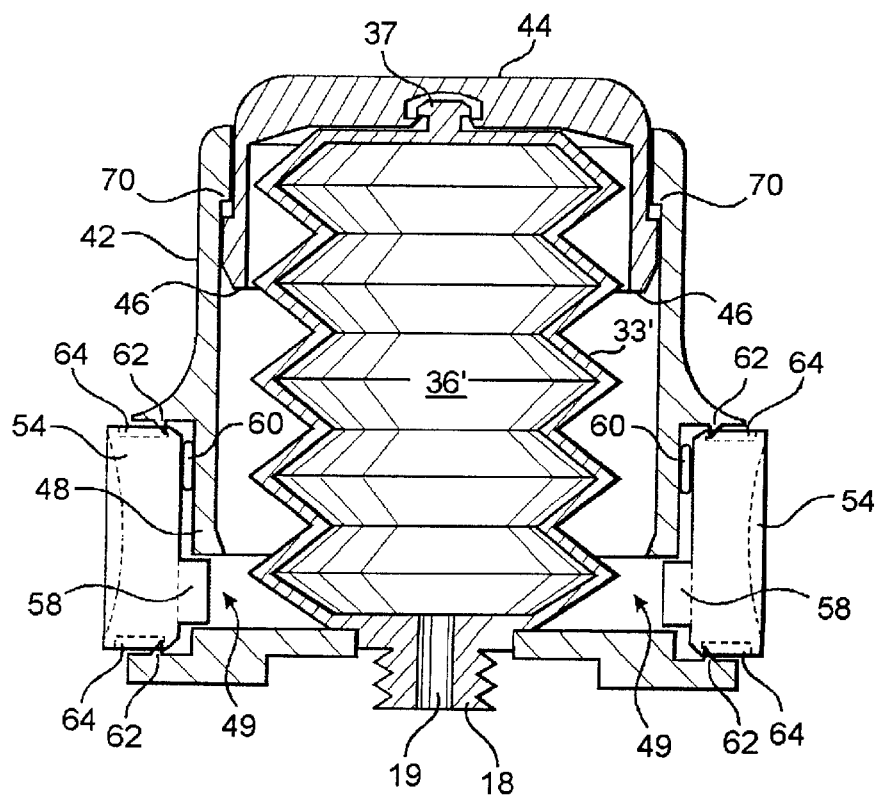
FIG. 7 is a detailed sectional view of certain structural components of the embodiment of FIGS. 5 and 6 where a pressure regulating assembly thereof is shown in an expanded position.

Looking to FIGS. 5, 6 and 7, the present invention comprises yet another preferred embodiment of the sinus pain relief assembly, generally indicated therein as 10'. This embodiment of the sinus pain relief assembly 10' is similar to that of the previously recited preferred embodiment sinus pain relief assembly 10 in that the pressure regulating assembly is primarily defined by an expandable bellows 33' formed of a plastic or like flexible material which is normally biased outwardly into the expanded position shown in FIG. 7. The vacuum chamber 36' is defined on the hollow interior of the bellows 33' and the bellows 33' is movable selectively from the expanded position of FIG. 7 to the collapsed position of FIG. 6 so as to remove the majority of air from the vacuum chamber 36'. Once so removed, the seal 20 is engaged in sealing relation and surrounding disposition about the nose 210 and an outwardly spaced relation to the nostrils 220 of the user 200.

Figure 6A:
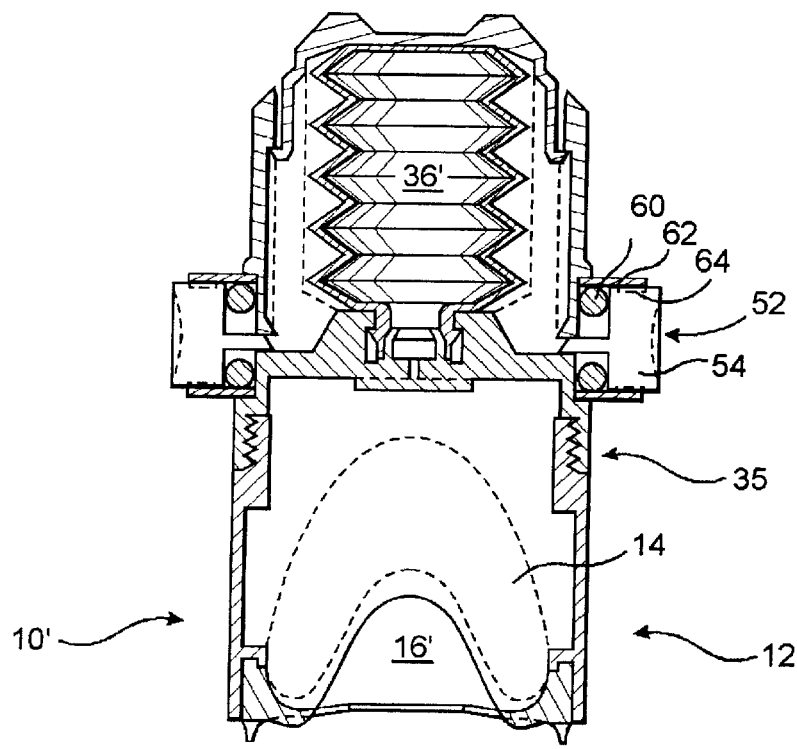
FIG. 6A is a detailed sectional view of a variation of the embodiment of FIG. 5 including external perimeter threading to achieve detachment of the mask.

Additional structural features of the preferred embodiment sinus pain relief assembly 10' include the existence of a housing generally indicated as 40 and including a somewhat sleeve like structure 42 disposed in surrounding, somewhat enclosing relation to the bellows 33' when it is either in its expanded position of FIG. 7 or its collapsed position of FIG. 6. Further, the sinus pain relief assembly 10' includes a positioning member 44 secured to the outer or distal end as at 34' of the bellows 33'. For example, although not necessary as in FIG. 6A, an integrally formed projection as at 37 of FIG. 5 may be used if desired. The positioning member 44 is connected to the bellows 33' so as to travel therewith and accomplish the selective positioning of the bellows 33' from its expanded position of FIG. 7 to its collapsed position of FIG. 5 and 6. Such disposition is accomplished similarly to that of FIG. 10 in that a single finger of the user may be positioned on the exterior of the positioning member 44 and an inwardly directed force is applied thereto in accordance with directional arrow 45.

Also preferably included with the sinus pain relief assembly 10' of the present invention is a locking assembly. The locking assembly comprises one or more first locking components 46 integrally formed on the positioning member 44 and movable therewith. A second locking component comprises one or more inwardly directed shoulders as at 48 inwardly extending into the path of travel of the first locking components 46 of the positioning member 44. With reference to FIG. 6, inwardly directed force applied to the positioning member 44 will serve to position it until the second locking members 48 removably but lockingly engage the first locking component 46 on the positioning member as shown. It should be apparent that the bellows 33' is therefore retained within the collapsed position. The seal 20 is then applied in sealing engagement with the face and in surrounding relation to the nose 210 and nostrils 220 of the user 200. When properly sealed and when the hollow interior 16 of the body portion 14 and the vacuum chamber 36' are in direct fluid communication with one another a release mechanism generally indicated as 52 is activated. Such activation occurs by an inwardly directed force being exerted on release members 54 by appropriately positioned fingers 55 and 56 of the user 200. Such inwardly directed force in accordance with directional arrows 57 will cause fingers 58 attached to the members 54 to engage the first locking components 46 on the positioning member 44. This will cause an inward flexing of the first locking members 46 and a disengagement of these locking members 46 from the second locking members 48. The inherent flexibility and structural bias of the bellows 33' will thereby cause the bellows to move outwardly into the expanded position shown in FIG. 7. A negative pressure will be created in the nasal cavity 28 (See FIG. 1) as air flows therefrom through the hollow interior 16 of the body portion 14 and through passage 19 into the interior of the vacuum chamber 36'. Operation of the release assembly 52 is facilitated through the provision of biasing members as at 60 serving to normally position the release members 54 in there outermost position as shown in FIG. 6. Projections 62 preferably integrally formed on the housing body 42 slide within the tracks or grooves integrally formed in the release member 54 so as to properly orient and position the release member 54 for operation as described above.

With reference to FIG. 7, one or more block members as at 70 are integrally formed on the housing body 42 and limit the outermost extension of the positioning member 44 through engagement with the first locking components 46 as clearly is disclosed.

Figure 8:
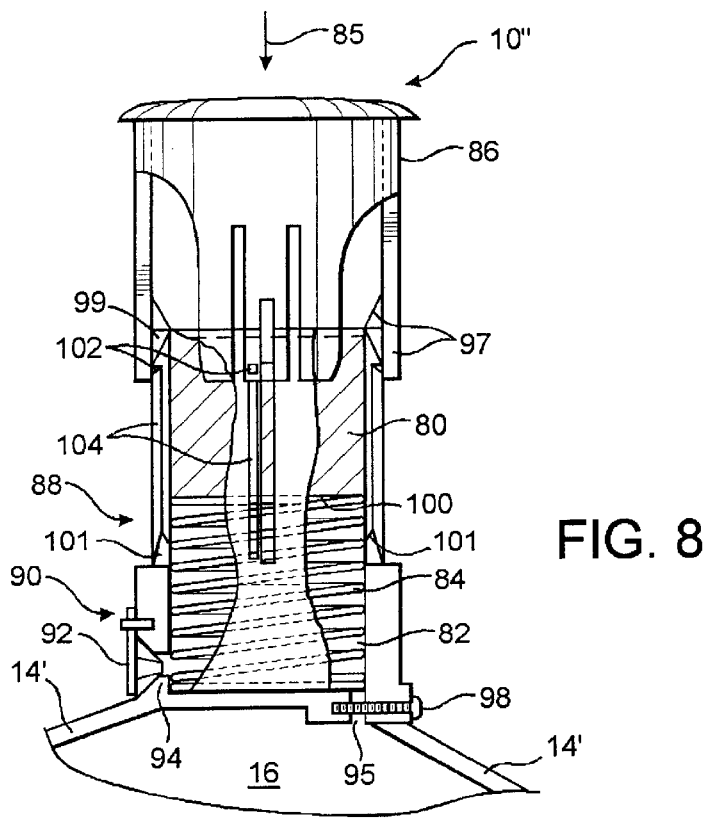
FIG. 8 is yet another preferred embodiment of the present invention.
Figure 9:
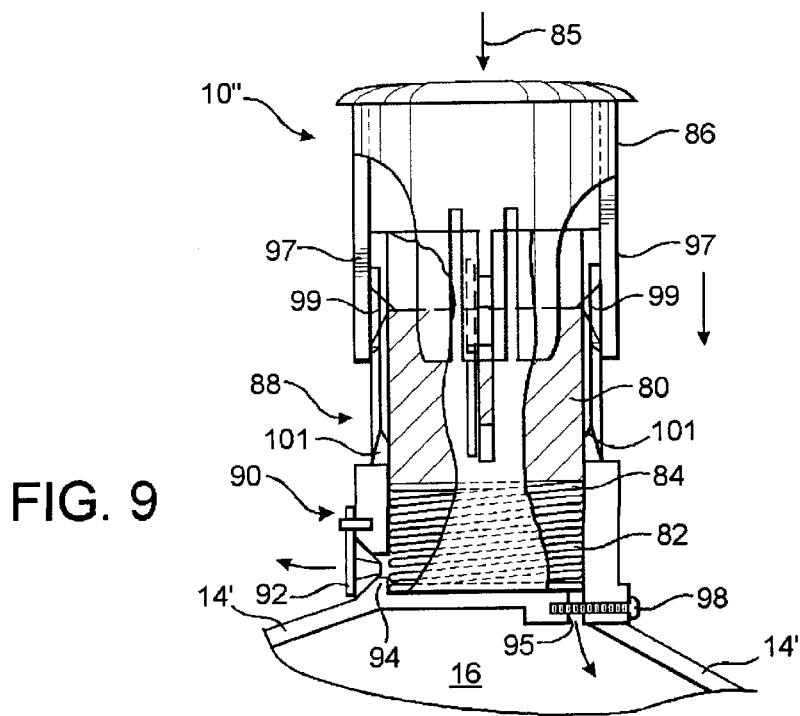
FIG. 9 is a sectional view in partial cutaway of the embodiment of FIG. 8 in a different operative position.

Yet another preferred embodiment of the sinus pain relief assembly 10" is shown in various operative positions in FIGS. 8–12. More specifically, the sinus pain relieving assembly 10" includes a movable vacuum piston 80 movably mounted within a vacuum chamber 82 and biased by a biasing spring 84 into its normally outer, expanded position, as shown in FIG. 8. The movement of the piston 80 is accomplished by manipulation of a positioning member 86 initially connected to an outermost end of the piston 80, as best shown in FIG. 8. The pressure regulating assembly includes a body 88 having a hollow interior which defines the vacuum chamber 82 and in which the piston 80 moves between the aforementioned expanded positions of FIG. 8 and the collapsed position of FIG. 11. A vent assembly 90 is formed on the housing 88 of the pressure regulating assembly and comprises a valve member 92 preferably in the form of a flap valve serving to normally seal a vent aperture 94. However, when the piston 80 is directed inwardly into the vacuum chamber 82 and into its collapsed position (See FIG. 11). Air normally within the vacuum chamber 82 will be exhausted through vent aperture 94 as the flap valve 92 is forced outwardly to release air pressure therein. The positioning member 86 is of course manipulated by an appropriate finger of the hand of the user to apply the force as indicated by directional arrow 85. Similarly, a vacuum passage as at 95 serves to establish direct fluid communication between the vacuum chamber 82 and the hollow interior 16' of the body portion 14' as well as the interior of the nasal cavity 28 once the seal 20 (not shown) is in its aforementioned sealed engagement on the face of the user. An adjusting screw is disposed and structured to regulate the size of vacuum passage 95.

Other structural features of the additional embodiment of the sinus pain relief assembly 10" includes a lock and unlock components in the form of elongated arms as at 97 being formed of a flexible material and integrally attached to the positioning member 86. In addition, piston engagement tangs as at 99 are also integrally formed on the lock and unlocking arms 97 so as to travel therewith. In the position shown in FIG. 8 these tangs 99 engage the outermost end of the piston 80 and force it downwardly from the expanded position of FIG. 8 into the collapsed position of FIG. 11. Such tangs 99 travel in piston engaging tang slots 100 formed in the housing 88 of the pressure regulating assembly for guidance of the positioning member 85 during the reciprocal travel during its stroke. Further, an unlocking shoulder as at 101 is also included and integrally formed on the housing 88 and disposed in interruptive relation to the downward travel of the piston engaging tangs 99. Once the shoulders 101 engage the tangs 99 the lock and unlocking arms 97 will be forced outwardly (See FIG. 11) causing the release of the positioning member 86 from the piston and an upward travel of the positioning member as well as the beginning upward travel of the piston 80. Upward travel into its expanded position of the piston 80 will be caused by the force exerted thereon will by the biasing spring 84.

Figure 10:
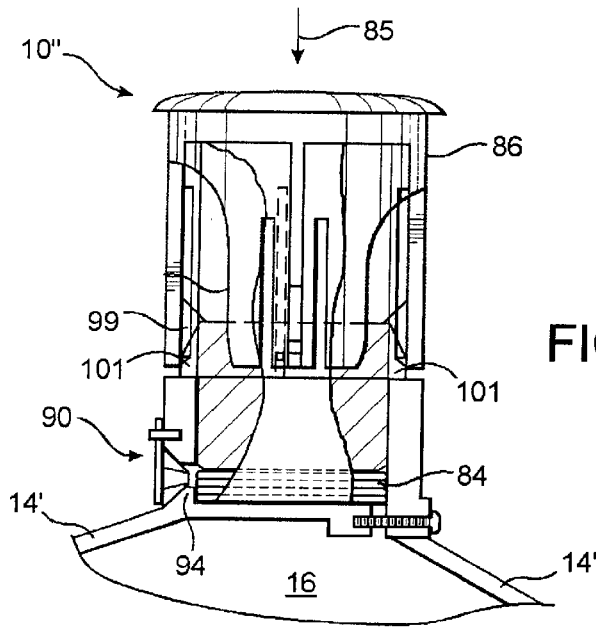
FIG. 10 is a sectional view in partial cutaway of the embodiment of FIGS. 8 and 9 in a different operative position.
Figure 11:
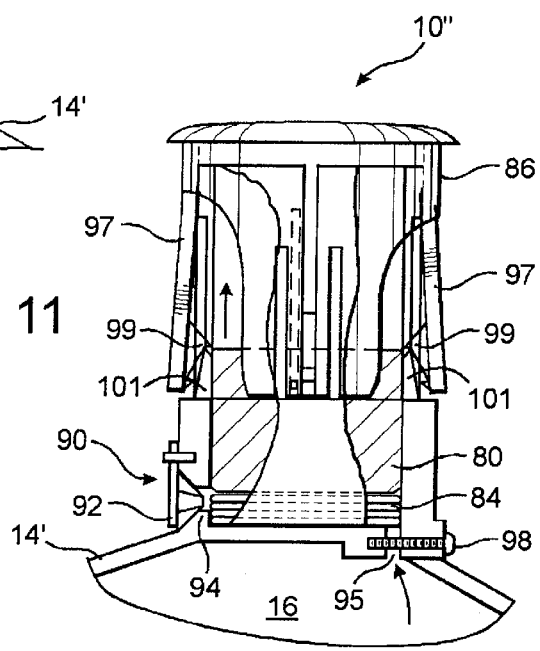
FIG. 11 is a sectional view in partial cutaway of the embodiment of FIGS. 8, 9 and 10 in a different operative position.
Figure 12:
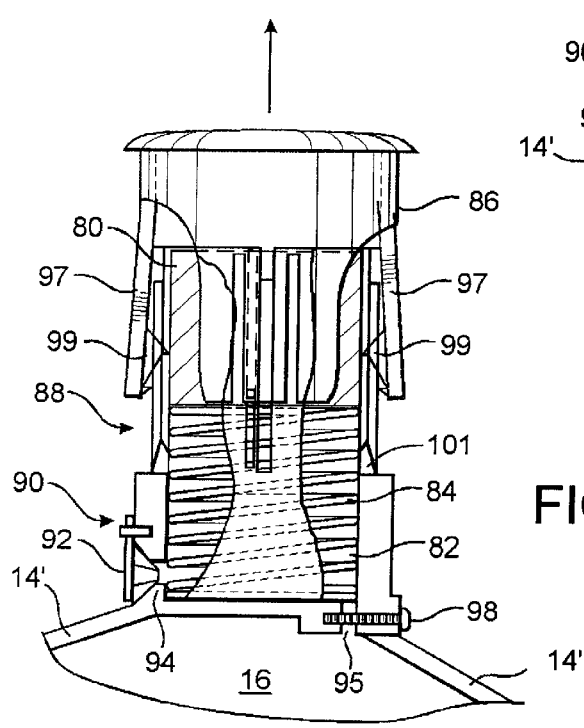
FIG. 12 is a sectional view in partial cutaway of the embodiments of FIGS. 8–11 in a different operative position.

An up lock 102 formed on the positioning member 86 is structured and disposed to travel within up lock grooves 104 formed on the housing 88 and serve to limit the outer extension of the positioning member 86 as best shown in FIG. 8. A thorough review of the various operative positions shown in FIGS. 8–12 show that a downward force 85 exerted on the positioning member 86 will cause a downward travel of the piston 80 into its collapsed position as shown in FIG. 10. The continued downward travel of the positioning member 86 will in turn cause an engagement of the unlocking shoulders 101 with the tangs 99 of the locking and unlocking arms 97. The positioning member 86 will therefor be disengaged from the piston allowing the upward travelling of the piston 80 due to the force exerted thereon by the biasing spring 84 and the eventual upward travel of the positioning member 86.

Figure 13:
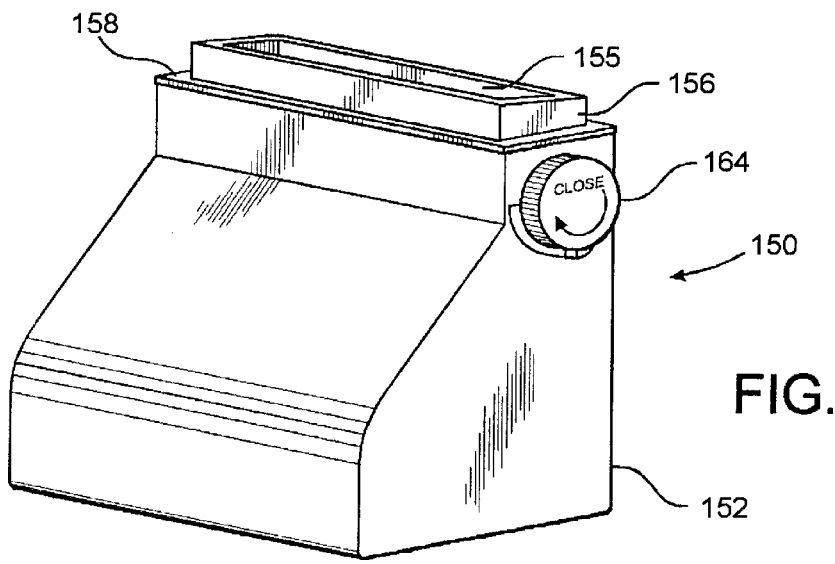
FIG. 13 is a perspective view of yet another preferred embodiment of the present invention relation to a hydrator assembly.
Figure 14:
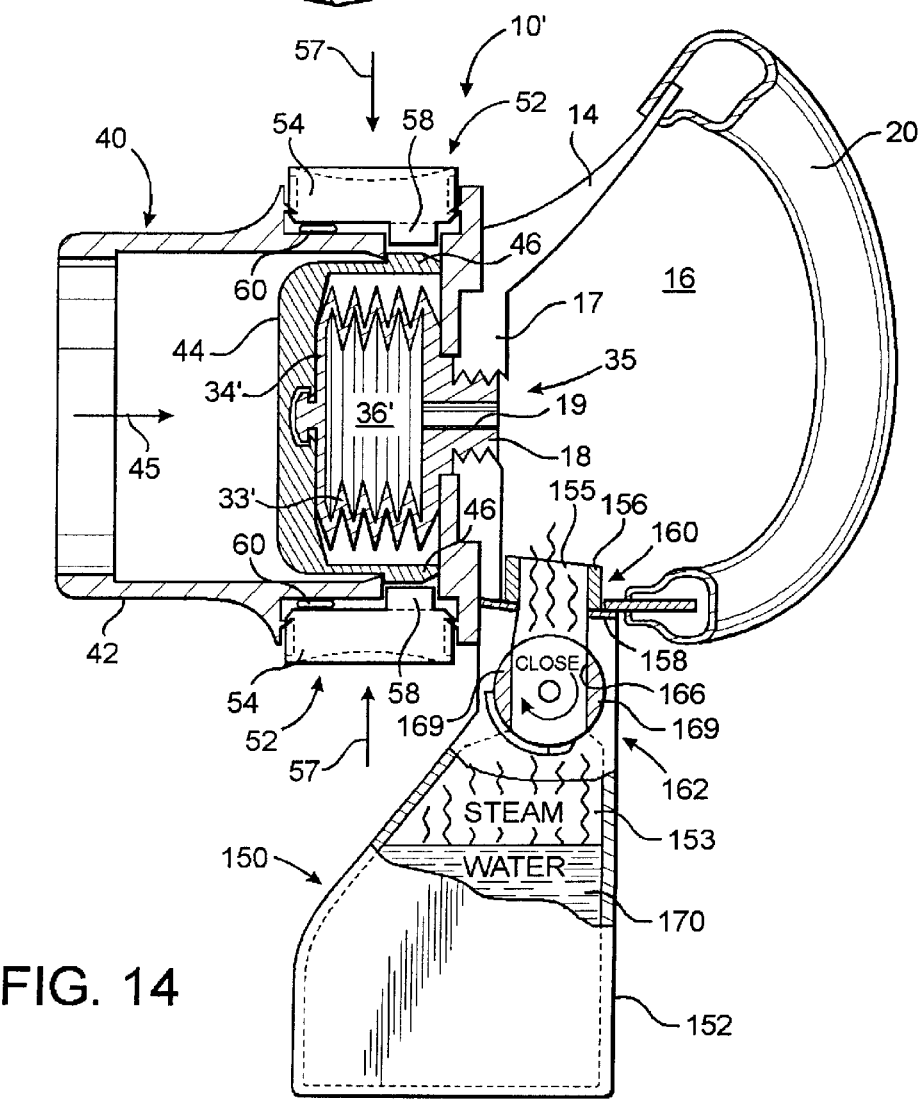
FIG. 14 is a sectional view in partial cutaway showing the hydrator assembly of FIG. 13 attached to the structural embodiment of FIG. 6.

Yet another preferred embodiment of the present invention is shown in FIGS. 13 and 14 wherein a hydrator assembly generally indicated as 150 includes a hydrator housing 152 having a hollow interior (See FIG. 14) 153. The upper end of the housing 152 has an opening as at 155 surrounded by a mating or connecting collar 156. A gasket or seal structure 158 is disposed in surrounding relation to the connecting collar 156 and is specifically adapted to engage an outer surface of the body portion 14' of the mask in order to establish sealing engagement therewith. The upper opening or aperture 155 communicates directingly with the hollow interior 16 of the body portion 14' in that the connecting or mating collar 156 passes through a specifically dimensioned and configured opening as at 160 integrally formed in the body portion 14'. When the hydrator assembly 150 is not being used or is disposed in detached relation to the body portion 14', a plug or like closure element (not shown for purposes of clarity) may be used to close the opening 160 in the body portion 14'.

The hydrator assembly 150 of the present invention also preferably includes a valve assembly 162 including an externally accessible knob 164 which may be selectively positioned between an opened and a closed position by the hand of the user or patient. When in the open position, as shown in FIG. 14, the valve structure 162 includes an integrally, interiorly formed passage 166 which is disposed to establish fluid communication between the interior 153 of the hydrator body 152 and the opening 155 in the upper end thereof. This of course establishes direct fluid communication with the hollow interior 16 of the body portion 14' and also with the nasal cavity and nasopharynx once the body portion 14' is properly applied to and sealed about the nose and nostrils of the user as best shown in FIG. 5.

In operation, prior to fitting the hydrator body 152 to the body portion 14', it is filled with hot water or saline solution as at 170, while the valve structure 162 is in its opened position. Once filled, the valve structure is moved to its closed position such that solid portions as at 169 of the valve structure 162 serve to block communication between 153 and the opening 155. With the valve in its closed position, the opening 155 is placed in direct communication with the hollow interior 16 of the body portion 14' by the insertion of the connecting collar 156 through the opening 160 and by establishing sealing engagement with the exterior of the body portion 14' due to the provision of the aforementioned gasket or seal structure 158. The pressure regulating assembly is then positioned into its lapsed position as shown in FIG. 14. Once in said position, the valve structure 162 is opened to the position shown in FIG. 14 and water vapor or steam is allowed to pass upwardly and into the hollow interior 16 of the body portion 14'. When adequate nasal cavity and/or nasopharynx pre-hydration has been achieved, the valve structure 162 is again disposed in its closed position. Following pre-hydration, the patient or user swallows and the bellows 33' is released to assume its expanded position and thereby create an initial negative pressure within the nasal cavity and nasopharynx.

Since many modifications, variations and changes in detail, such as the use of a small vacuum pump, can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
What is claimed is:

1. A non-invasive sinus pain relieving assembly comprising:
   a) a mask including a body portion having a substantially hollow interior and structured to be removably mounted on a face of a user, said body portion further including an outer end and an inner end disposed in spaced relation to one another,
   b) a seal disposed at said outer end of said body portion of said mask and extending substantially continuously about a periphery thereof,
   c) said seal being structured and disposed to form a sealing engagement with the face of the user, and being cooperatively dimensioned and configured with said body portion of said mask so as to surround a nose of the user in outwardly spaced relation to nostrils thereof,
   d) a pressure regulating assembly cooperatively coupled with said body portion generally at said inner end, said pressure regulating assembly including a vacuum chamber disposed in fluid communication with said hollow interior of said body portion,
   e) said pressure regulating assembly being selectively positionable between a collapsed position, defined by a reduced volume of air present within said vacuum chamber, and an expanded position, defined by an increased volume of air present within said vacuum chamber,
   f) said mask and vacuum chamber disposable in an operative position defined by said seal forming said sealing engagement with the face of the user and said vacuum chamber and hollow interior of said body portion concurrently being disposed in fluid communication with a nasal cavity and nasopharynx of the user so as to equalize pressure between the nasal cavity and the nasopharynx, and a middle ear and sinus cavities of the user, thereby relieving sinus pain and middle ear pressure,
   g) a disposition of said pressure regulating assembly from said collapsed position to said expanded position while the user swallows, defining a flow of air from said hollow interior of said body portion to said vacuum chamber and a reduction of pressure within the nasal cavity and nasopharynx,
   h) said pressure regulating assembly comprising a bellows formed of flexible material and including said vacuum chamber formed on an interior thereof, said bellows structured for selective positioning between said collapsed position and said expanded position, and
   i) said bellows removably coupled with said inner end of said body portion and being selectively positionable into a stored position; said stored position being defined by said pressure regulating assembly attached to said inner end of said body portion and extending inwardly therefrom into said hollow interior of said body portion.

2. A non-invasive sinus pain relieving assembly as in claim 1 wherein said pressure regulating assembly further comprises a positioning member cooperatively disposed with said bellows and movable therewith relative to said housing between said collapsed position and said expanded position.

3. As assembly as in claim 2 wherein said positioning member is cooperatively engaged with an outer end of said bellows and is movable therewith with in said housing upon an inwardly directed force being applied to said positioning member by the user.

4. A non-invasive sinus pain relieving assembly as in claim 2 further comprising a lock assembly formed at least in part on both said positioning member and said housing, said lock assembly structured to removably secure said bellows in said collapsed position upon a sufficient inwardly directed force being applied to said positioning member by the user.

5. A non-invasive sinus pain relieving assembly as in claim 4 wherein said lock assembly comprises a first portion and a second portion, said first portion being formed on said positioning member and being movable therewith, said second portion being formed on said housing in lockable engagement with said first portion, and said first and said second portions being selectively movable into and out of locking engagement with one another so as to removably secure said bellows in said collapsed position.

6. A non-invasive sinus pain relieving assembly as in claim 5 further comprising a release assembly mounted on said housing and selectively movable into engagement with said first portion for movement of said first portion relative to said second portion, out of locking engagement therewith.

7. A non-invasive sinus pain relieving assembly as in claim 6 wherein said release assembly comprises at least one release member externally accessible and movably mounted on said housing between an outwardly extended position and an inwardly extended position, said one release member normally biased into said outwardly extended position and movable into said inwardly extended position and into displacing engagement with said first portion of said lock assembly upon a force being exerted on said positioning member by a hand of the user.

8. A non-invasive sinus pain relieving assembly as in claim 4 further comprising a release assembly externally accessible and movably mounted on said housing into displacing engagement with said lock assembly for displacement of said bellows from said collapsed position upon a force being exerted on said release assembly by the user.

9. A non-invasive sinus pain relieving assembly as in claim 8 wherein said pressure regulating assembly comprises a piston movably mounted within said vacuum chamber and selectively positionable between said collapsed position and said expanded position and including a biasing spring engaging and normally biasing said piston into said expanded position.

10. A non-invasive sinus pain relieving assembly as in claim 9 further comprising a vent assembly mounted on said housing and disposed and structured to regulate fluid flow between said vacuum chamber and an exterior of said housing upon movement of said piston within said vacuum chamber between said collapsed position and said expanded position.

11. A non-invasive sinus pain relieving assembly as in claim 10 wherein said vent assembly includes a valve structure movably mounted on said housing and structured to restrict airflow into said vacuum chamber from an exterior of said housing when said piston moves from said collapsed position to said expanded position; said valve structure further structured to facilitate airflow from said vacuum chamber to an exterior of said housing when said piston moves from said expanded position to said collapsed position.

12. A non-invasive sinus pain relieving assembly as in claim 10 wherein said pressure regulating assembly further comprises a positioning member engaging said piston and movable therewith relative to said housing between said expanded position and said collapsed position upon an inwardly directed force being applied to said positioning member by a hand of the user and against a biasing force exerted on said piston by said biasing spring.

13. A non-invasive sinus pain relieving assembly as in claim 12 further comprising said release assembly at least partially mounted on both said positioning member and said housing and structured to release travel of said piston relative to said positioning member from said collapsed position to said expanded position.

14. A non-invasive sinus pain relieving assembly as in claim 1 wherein said seal is formed from a moldable material structured to conform to the user's facial contours.

15. A non-invasive sinus pain relieving assembly as in claim 14 wherein the moldable material includes hydroplastic.

16. A non-invasive sinus pain relieving assembly comprising:
  a) a mask including a body portion having a substantially hollow interior and structured to be removably mounted on a face of a user, said body portion further including an outer end and an inner end disposed in spaced relation to one another,
  b) a seal disposed at said outer end of said body portion of said mask and extending substantially continuously about a periphery thereof,
  c) said seal being structured and disposed to form a sealing engagement with the face of the user, and being cooperatively dimensioned and configured with said body portion of said mask so as to surround a nose of the user in outwardly spaced relation to nostrils thereof,
  d) a pressure regulating assembly cooperatively coupled with said body portion generally at said inner end, said pressure regulating assembly including a vacuums chamber disposed in fluid communication with said hollow interior of said body portion,
  e) said pressure regulating assembly being selectively positionable between a collapsed position, defined by a reduced volume of air present within said vacuum chamber, and an expanded position, defined by an increased volume of air present within said vacuum chamber,
  f) said mask and vacuum chamber disposable in an operative position defined by said seal forming said sealing engagement with the face of the user and said vacuum chamber and hollow interior of said body portion concurrently being disposed in fluid communication with a nasal cavity and nasopharynx of the user so as to equalize pressure between the nasal cavity and the nasopharynx, and a middle ear and sinus cavities of the user, thereby relieving sinus pain and middle ear pressure,
  g) a hydrator assembly removably connected in direct fluid communication with said hollow interior of said body portion of said mask, and
  h) said hydrator assembly including a hydrator housing having an interior chamber structured to receive and maintain heated liquid therein, an opening formed in an upper portion of said hydrator housing and disposed in communicating relation to said hollow interior of said body portion.

17. A non-invasive sinus pain relieving assembly as in claim 16 wherein said hydrator assembly further comprises a valve structure mounted on said hydrator housing and selectively positionable to regulate fluid flow from said interior chamber to said hollow interior of said body portion.

18. A non-invasive sinus pain relieving assembly as in claim 17 wherein said hydrator assembly further includes a seal member positioned in substantially surrounding relation to said opening on an exterior of said hydrator housing, said seal member disposed and structured to establish sealing engagement with an exterior surface of said body portion of said mask.

19. A non-invasive sinus pain relieving assembly comprising:
  a) a mask including a body portion having a substantially hollow interior and structured to be removably mounted on a face of a user, said body portion further including an outer end and an inner end disposed in spaced relation to one another,
  b) a seal disposed at said outer end of said body portion of said mask and extending substantially continuously about a periphery thereof,
  c) said seal being structured and disposed to form a sealing engagement with the face of the user, and being cooperatively dimensioned and configured with said body portion of said mask so as to surround a nose of the user in outwardly spaced relation to nostrils thereof,
  d) a pressure regulating assembly cooperatively coupled with said body portion generally at said inner end, said pressure regulating assembly including a vacuum chamber disposed in fluid communication with said hollow interior of said body portion,
  e) said pressure regulating assembly being selectively positionable between a collapsed position, defined by a reduced volume of air present within said vacuum chamber, and an expanded position, defined by an increased volume of air present within said vacuum chamber,
  f) said mask and vacuum chamber disposable in an operative position defined by said seal forming said sealing engagement with the face of the user and said vacuum chamber and hollow interior of said body portion concurrently being disposed in fluid communication with a nasal cavity and nasopharynx of the user so as to equalize pressure between the nasal cavity and the nasopharynx, and a middle ear and sinus cavities of the user, thereby relieving sinus pain and middle ear pressure, g) a disposition of said pressure regulating assembly from said collapsed position to said expanded position while the user swallows, defining a flow of air from said hollow interior of said body portion to said vacuum chamber and a reduction of pressure within the nasal cavity and nasopharynx, h) said pressure regulating assembly coupled with said inner end of said body portion and being selectively positionable into a stored position; said stored position being defined by said pressure regulating assembly attached to said inner end of said body portion and extending inwardly therefrom into said hollow interior of said body portion.

20. A non-invasive sinus pain relieving assembly comprising:

a) a mask including a body portion having a substantially hollow interior and structured to be removably mounted on a face of a user, said body portion further including an outer end and an inner end disposed in spaced relation to one another, b) a seal disposed at said outer end of said body portion of said mask and extending substantially continuously about a periphery thereof, c) said seal being structure and disposed to form a sealing engagement with the face of the user and being cooperatively dimensioned and configured with said body portion to surround and isolate a nose and nostrils from the mouth of the user, d) a pressure regulating assembly cooperatively coupled with said body portion generally at said inner end, said pressure regulating assembly including a vacuum chamber disposed in fluid communication with said hollow interior of said body portion, e) said pressure regulating assembly being selectively positionable between a collapsed position, defined by a reduced volume of air present within said vacuum chamber, and an expanded position, defined by an increased volume of air present within said vacuum chamber, f) said mask and vacuum chamber disposable in an operative position defined by said seal forming said sealing engagement with the face of the user and said vacuum chamber and hollow interior of said body portion concurrently being disposed in fluid communication with a nasal cavity and nasopharynx, and a middle ear and sinus cavities of the user, thereby relieving sinus pain and middle ear pressure, and g) said pressure regulating assembly further comprising a positioning member engaging an outer end of said pressure regulating assembly and movable therewith between said expanded position and said collapsed position upon an inwardly directed force being applied to said positioning member by the user.

21. A non-invasive sinus pain relieving assembly comprising:

a) a mask including a body portion having a substantially hollow interior and structured to be removably mounted on a face of a user, said body portion further including an outer end and an inner end disposed in spaced relation to one another, b) a seal disposed at said outer end of said body portion of said mask and extending substantially continuously about a periphery thereof, c) said seal being structured and disposed to form a sealing engagement with a face of the user and being cooperatively configured and disposed with said body portion to surround and isolate a nose and nostrils from the mouth of the user, d) a pressure regulating assembly cooperatively coupled with said body portion generally at said inner end, said pressure regulating assembly including a vacuum chamber disposed in fluid communication with said hollow interior of said body portion, e) said pressure regulating assembly being selectively positionable between a collapsed position, defined by a reduced volume of air present within said vacuum chamber, and an expanded position, defined by an increased volume of air present within said vacuum chamber, and f) said mask and vacuum chamber disposable in an operative position defined by said seal forming said sealing engagement with the face of the user and said vacuum chamber and hollow interior of said body portion concurrently being disposed in fluid communication with a nasal cavity and nasopharynx of the user so as to equalize pressure between the nasal cavity and the nasopharynx, and a middle ear and sinus cavities of the user, thereby relieving sinus pain and middle ear pressure.

22. A non-invasive sinus pain relieving assembly as in claim 21 wherein disposition of said pressure regulating assembly from said collapsed position to said expanded position while the user swallows, defines a flow of air from said hollow interior of said body portion to said vacuum chamber and a reduction of is pressure within said nasal cavity and nasopharynx.

23. A non-invasive sinus pain relieving assembly as in claim 22 wherein said pressure regulating assembly comprises a bellows formed of flexible material and including said vacuum chamber formed on an interior thereof, said bellows structured for selective positioning between said collapsed position and said expanded position.

24. A non-invasive sinus pain relieving assembly as in claim 23 wherein said bellows is connected to and extends outwardly from said inner end of said body portion of said mask in an externally accessible position relative to said body portion of said mask, and said bellows is structured to be affirmatively movable from said expanded position to said collapsed position by direct contact and force being applied by the user.

25. A non-invasive sinus pain relieving assembly as in claim 23 wherein said bellows is removably coupled with said inner end of said body portion and is selectively positionable into a stored position; said stored position being defined by said bellows attached to said inner end of said body portion and extending inwardly therefrom into said hollow interior of said body portion.

* * * * *